(12) United States Patent
Herrmann et al.

(10) Patent No.: US 9,133,485 B2
(45) Date of Patent: Sep. 15, 2015

(54) METHODS AND MATERIALS FOR THE REPRODUCIBLE GENERATION OF HIGH PRODUCER CELL LINES FOR RECOMBINANT PROTEINS

(75) Inventors: Andreas Herrmann, Allschwil (CH); Harry Abts, Oberursel (DE); Benedikt Greulich, Rheine (DE)

(73) Assignee: Celonic AG, Basel (CH)

(*) Notice: Subject to any disclaimer, the term of this patent is extended or adjusted under 35 U.S.C. 154(b) by 832 days.

(21) Appl. No.: 12/933,426

(22) PCT Filed: Mar. 27, 2009

(86) PCT No.: PCT/EP2009/002266
§ 371 (c)(1),
(2), (4) Date: Sep. 19, 2010

(87) PCT Pub. No.: WO2009/118192
PCT Pub. Date: Oct. 1, 2009

(65) Prior Publication Data
US 2011/0008895 A1 Jan. 13, 2011

Related U.S. Application Data

(60) Provisional application No. 61/040,315, filed on Mar. 28, 2008.

(30) Foreign Application Priority Data

Mar. 28, 2008 (EP) .................................... 08006023

(51) Int. Cl.
C12N 15/87 (2006.01)
C12N 15/00 (2006.01)
C12N 15/90 (2006.01)

(52) U.S. Cl.
CPC .......... C12N 15/907 (2013.01); *C12N 2800/30* (2013.01); *C12N 2800/80* (2013.01); *C12N 2830/42* (2013.01)

(58) Field of Classification Search
CPC .................................................. C12N 15/907
USPC ........................................................... 435/463
See application file for complete search history.

(56) References Cited

U.S. PATENT DOCUMENTS

| 2001/0032341 A1 | 10/2001 | Bode et al. |
| 2005/0032223 A1 | 2/2005 | Dujon et al. |
| 2006/0014264 A1 | 1/2006 | Sauer et al. |

FOREIGN PATENT DOCUMENTS

| EP | 11405908 | 4/2004 |
| WO | 91/09957 | 7/1991 |
| WO | 92/15694 | 9/1992 |
| WO | 96/30498 | 10/1996 |
| WO | 2004/029284 | 4/2004 |

OTHER PUBLICATIONS

Belfort, Marlene et al., Nucleic Acids Res. 25 (1997) 3379-3388.
Puttini et al., J. Biotechnol. 116 (2005) 145-151.
Sorrell, et al., Biotech. Adv. 23 (2005), 431-469.
International Search Report and Written Opinion, International Application No. PCT/EP2009/002266, Jun. 3, 2009.
International Preliminary Examination Report, International Application No. PCT/EP2009/002266, Jun. 10, 2010.
Communication from the European Patent Office in European Patent Application No. 08006023.9-2406, Sep. 30, 2008.

*Primary Examiner* — Christopher M Babic
*Assistant Examiner* — Kelaginamane T Hiriyanna
(74) *Attorney, Agent, or Firm* — Michael Fedrick; Loza & Loza, LLP

(57) ABSTRACT

The invention lies in the field of production of recombinant gene products in eukaryotic cells. The invention refers to methods and materials for the fast and reproducible generation of production cells lines suitable for large scale production of recombinant gene products. The invention encompasses specific vector systems, genetic engineered host-cells and methods of use.

Figure 1:
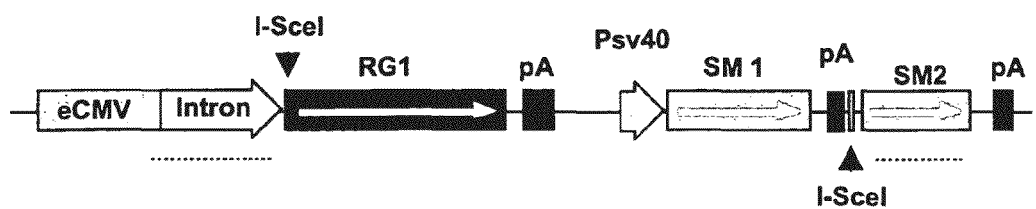

23 Claims, 10 Drawing Sheets

SEQUENCE LISTING

<160> NUMBER OF SEQ ID NOS: 1

<210> SEQ ID NO 1
<211> LENGTH: 18
<212> TYPE: DNA
<213> ORGANISM: Artificial
<220> FEATURE:
<223> OTHER INFORMATION: oligonucleotide

<400> SEQUENCE: 1
tagggataac agggtaat                                                   18

METHODS AND MATERIALS FOR THE REPRODUCIBLE GENERATION OF HIGH PRODUCER CELL LINES FOR RECOMBINANT PROTEINS

CROSS-REFERENCE TO RELATED APPLICATIONS

This application is the U.S. national stage of International Patent Application No. PCT/EP2009/002266, filed on Mar. 27, 2009 and entitled "METHODS AND MATERIALS FOR THE REPRODUCIBLE GENERATION OF HIGH PRODUCER CELL LINES FOR RECOMBINANT PROTEINS," which claims the benefit of priority from US Provisional Patent Application No. 61/040,315, filed on Mar. 28, 2008, and from European Patent Application No. 08006023.9, also filed on Mar. 28, 2008. The disclosures of the foregoing applications are incorporated herein by reference in their entirety.

SEQUENCE LISTING

The entire content of a Sequence Listing titled "Sequence_Listing.txt," created on Aug. 16, 2010 and having a size of 0.5 kilobytes, which is being submitted herewith in electronic form in connection with the present application, is hereby incorporated by reference herein in its entirety.

1. Field of the Invention

The invention lies in the field of production of recombinant gene products in eukaryotic cells. Particularly, the invention refers to methods and materials for the fast and reproducible generation of high-yield eukaryotic production cells lines suitable for large-scale production of recombinant gene products. The invention encompasses specific vector systems, characterized, genetic engineered host-cells and methods of use.

2. Background of the Invention

The CHO cell-line is one of the most widely used host cell for production of biopharmaceuticals. Classically, the host cell is transfected with an expression construct containing a gene of interest (GOI) coding for a recombinant gene product, e.g. a protein, and a selection marker such as an antibiotic, e.g. a neomycine or methotrexate resistance gene. In a small portion of the host-cells the expression construct is randomly introduced in the genom by non-homologous recombination. These stably transfected cells are selected under selection pressure of the antibiotic compound. In order to get a regulatory compliant single cell derived cell-line, a subcloning step by limited dilution is subsequently performed. Although several hundreds of single cell derived clones are analyzed, the expression level was often still weak, which requires the optimization of transfection procedures or the amplification of initially integrated copies of the expression construct, e.g. by increasing concentration of methotrexate or another amplifying system. The whole procedure takes at least 6 months, sometimes up to a year.

The major problem with this approach is the random nature of the integration event. The surrounding genomic DNA has a major effect on the translational activity of integrated expression construct ("position effect"). Due to the stochastic nature of this non-homologous integration process, the integration cannot be directed to loci with a high transcriptional activity (transcriptional hot spots). Since the majority of mammalian DNA is non-coding and even the coding-part is only to a small proportion transcriptionally active, most integration events will lead to a low expression of the transgene. In summary the random integration of an expression construct will lead to wide variation in the expression levels of the transgene with only a fraction of cells showing high-level expression.

In order to circumvent the necessary laborious screening process and to decrease the time for the generation of a high producer cell-line, a system for the targeted insertion of any GOI into a hot spot of expression of the genome of a host cell would be desirable.

In order to repetitively introduce a GOI into this site, the identified site may be supplemented with sequences that allow the insertion by sequence specific recombinases such as Cre or FLP. The use of Flp for such modifications is described in WO 92/15694 and with modifications for the marker-free repetitive DNA expression cassette exchange in US2001/0032341. The use of Cre for the modification of the genome in plant cells was described in WO 91/09957 and with further modifications in US2006/0014264A1.

Both recombinases are dependent on specific recognition sites which have to be introduced first into the genome at an appropriate genomic localisation. In the case of transgenic animals this is achieved by homologous recombination.

In order to use these specific recombinases for the generation of a production cell line, the major problem is to identify a suitable gene for insertion of recognition sites by homologous recombination. This gene needs to be highly transcribed, but at the same time should not essential for the cell. The immunoglobulin locus in a myeloma- or hybridom-cell would be an example of such an appropriate locus. The production of antibodies by use of a combination of homologous recombination and sequence-specific recombination using Cre is described in WO 96/30498. A similar approach is described as high yield general expression system in EP11405908A1.

Although applicable, these approaches are restricted to known, non-essential, highly expressed cellular genes in the respective host-cell. In addition spontaneous homologous recombination is a rare event and its efficiency depends on the respective site. To reach a high efficiency large homologue sequences have to be used, where isogenic sequences been most effective. Therefore the use of this approach in host from which limited sequence information (like hamster) is available, will limited its applicability.

In order to identify randomly genomic loci that allow a high expression level, it has been described to introduce at the target site a vector containing a reporter gene and the required recognition sites for the used recombinase (WO 2004/029284A3). While the reporter gene allows the characterization of the expression capacity of the randomly tagged integration site, the recognition sites allow the exchange of the reporter against the GOI.

Puttini et al. (J. Biotechnol. 116 (2005), 145-151) disclose a method for targeted, double-stranded break-mediated transgenesis in a cell line. Thereby, host cells expressing a target gene are obtained. The targeting vector comprises a single meganuclease recognition site. A low targeting efficiency of $2.5 \times 10^{-6}$ (10 clones/$2 \times 10^7$ cells with 20% transfection efficiency) is reported. Thus, this document does not provide a reliable method for obtaining high-producing host cells.

WO 2004/029284 describes a method for the generation of a producer host cell using a site-specific recombination catalysed by FLP recombinase. The resulting expression cell lines still contain FLP recombinase recognition sites, in some cases within the coding sequence after introduction of the gene of interest. This results in a decreased stability of the producer cell line. The document also suggests group II introns as alternative recombination recognition sites, however, without disclosing experimental evidence therefor.

Meganuclease recognition sites group I intron encoded homing endonucleases are not disclosed.

Sorrel & Kolb (Biotech. ADV 23 (2005), 431-469) describe a site-specific modification of mammalian genomes by homologous recombination using targeting vectors having a single recognition site for the meganuclease I-Sce-1. The integration of the target/replacement vector occurs via targeted homologous recombination and not via random integration.

Belfort & Roberts (Nucleic Acids Res. 25 (1997), 3379-3388) describe homing endonucleases including group I and group II intron-encoded molecules.

With all these approaches the efficiency of the exchange reaction is depending on the efficiency of the used recombinase. In addition the random selected locus might have a good transcriptional activity, but it might not support efficient recombination by the used recombinase. In order to identify an appropriate integration locus this approach will require additional screening effort. A further potential obstacle in the use of such recombinases is the presence of pseudo-recognition sites within the genome of the desired host-cell. These pseudo-recognition sites could lead to unwanted recombination events. This will lead to a reduce efficiency of the system and to potentially genetic modified cells with undesirable phenotype. Again, a screening to identify the most suitable cells has to be done. Although this approach deems functional, its efficiency and universal applicability in the generation of a high-yield production cell will be low.

Taken together there is a still a need for a fast, efficient and universal system for the generation of a high-yield eukaryotic production cells line with proven capabilities for the large scale production of recombinant proteins.

The present invention discloses methods and material in order to fulfil this demand.

3. SUMMARY OF THE INVENTION

The present invention describes methods and materials relating to a wildcard-strategy for the generation of high-yield eukaryotic cell-lines for the production of biopharmaceuticals involving the site-specific introduction of an expression cassette comprising a GOI into a pre-formed and characterized host cell-line (the wildcard cell). The wildcard cell has been selected for properties necessary for large scale production in dynamic culture systems. It is generated by randomly introducing a tagged reporter cassette into the genome of a starting cell line and by characterising the expression capacity of the integration site. By exchanging the reporter against a gene of interest (GOI), a producer cell line capable of efficiently expressing a desired gene product is obtained.

As source for the GOI an exchange vector is used, which does not allow strong expression of the GOI by itself and preferably does not confer a selectable property to the transfected cells.

Unlike described systems the wildcard-strategy does not use recombinases in order to mediated the exchange of expression cassettes. The exchange of the first reporter gene and selection marker is mediated by double strand break (DSB) induced homologous recombination. In order to induce the DSB at the desired genomic position the targeted locus contains as specific tag one or two recognition sites for a rare DSB-mediating enzyme, e.g. a rare cutting meganuclease or homing endonuclease (HE) such as I-SceI. The HE is brought into the cells and confers the restriction of the recognition sites at the defined position. The repair of the DSB break is performed at a high frequency by the endogenous repair-mechanisms of the cell. The parallel transfected exchange vector serves as repair matrix due to sequences homologous to the flanking regions of the exchanged cassette.

Such a new host cell facilitates the cloning of a GOI into predetermined genomic expression hot spots within short time in order to get reproducible, highly efficient production cell-lines for recombinant gene products, particularly for recombinant proteins.

The method includes the following steps:
  Random integration of a target vector containing a selectable marker, a quantifiable reporter gene and recognition sites for mediating DSB-induced homologous recombination.
  Selection of a universal host cell line ("wildcard"-cell) with preferentially a single integrated copy of the target vector at a transcriptionally active locus, as judged by the reporter gene.
  Exchange of the reporter gene and first selectable marker against a gene of interest (GOI) and simultaneously generation of at least one additional selectable marker by DSB-induced homologous recombination involving an exchange vector with the required elements as repair-matrix.

The exchange process in the universal wildcard-host-cell can be performed for other GOIs and will deliver each time a production cell with predictable, high expression levels, quality of the product (i.e. glycosylation) and growth properties allowing large scale production of the gene product, e.g. of a protein.

The method preferentially allows the production of any recombinant protein. The produced protein could be an enzyme, in particular a protease, protease inhibitor, hormone, cytokine, receptor with and without transmembrane or intracellular domains (i.e. membrane bound or soluble), full-length antibodies or antibody domains. In particular the produced protein could resemble a fusion protein combining parts or domains of the mentioned proteins.

The present system allows therefore the generation of high-producer cells necessary for the efficient and economically production of biopharmaceuticals.

It offers several advantages:
  Time saving: a stable production cell-line could be obtained within a few weeks starting with a pre-made wildcard cell-line.
  Due to integration into pre-identified expression hot spots, the expression level of the production cell-line can be predicted more reliable and could be reached reproducible for different GOIs.
  High efficiency since only cells expressing the GOI will be obtained after the exchange.
  No additional integration of dispensable vector sequences during site-specific integration.
  Production of material for proof of concept experiments could be done within a few months. There will be no change in product quality at later development phases because a homogenous and genetically identical cell population will be available from the very beginning.

Thus, a first aspect of the present invention is a method for the generation of a producer cell for the production of recombinant gene products, particularly polypeptides comprising the steps
  (a) providing a target vector comprising
    (i) a reporter gene (RG1) operatively linked to a first expression control sequence (P1),
    (ii) a first selection marker gene (SM1) operatively linked to a second expression control sequence (P2), (iii) a second non-functional selection marker gene (SM2) without operative linkage to an expression control sequence,
wherein sequence (i) is located in the 5'-position, sequence (ii) is located between (i) and (iii) and sequence (iii) is located in the 3'-position,
(iv) a first and a second recognition site for a double-strand break mediating enzyme, wherein the first recognition site is located between the first expression control sequence (P1) and the first reporter gene (RG1) and the second recognition site is located between sequence (ii) and sequence (iii),
(b) introducing the target vector in a host cell under conditions in order to allow random integration of the target vector into the genome of the host cell,
(c) selecting a host cell having stably integrated the target vector and showing transcriptional activity, preferably high and stable transcriptional activity of the RG1,
(d) providing an exchange vector comprising:
(i) a gene of interest (GOI), and
(ii) an inactive second selection marker gene (ΔSM2) operatively linked to a third expression control sequence (P3),
wherein the exchange vector comprises a first 5'-homologous sequence and a second 3'-homologous sequence, which allow recombination with sequences of the target vector,
(e) introducing the exchange vector into a host cell obtained in step (c) under conditions to allow a double strand break at the first and/or second recognition site, preferably at the first and second recognition site, as defined in (a)(iv) and an integration of the exchange vector into the genome of the host cell by double-strand break-mediated homologous recombination,
whereby the inactive second selection marker (ΔSM2) is activated by an integration of the exchange vector,
(f) selecting a producer cell having integrated the exchange vector by homologous recombination with the integrated target vector, wherein the producer cell expresses the GOI.

A further aspect of the present invention is a method for generating an universal host-cell (wildcard cell) allowing the fast production of high-yield production cell lines suitable for large scale production of recombinant gene products. This method comprises
(a) providing a target vector comprising
(i) a reporter gene (RG1) operatively linked to a first expression control sequence (P1),
(ii) a first selection marker gene (SM1) operatively linked to a second expression control sequence (P2),
(iii) a second non-functional selection marker gene (SM2) without operative linkage to an expression control sequence,
wherein sequence (i) is located in the 5'-position, sequence (ii) is located between (i) and (iii) and sequence (iii) is located in the 3'-position,
(iv) a first and a second recognition site for a double-strand break mediating enzyme, particularly a meganuclease, wherein the first recognition site is located between the first expression control sequence (P1) and the first reporter gene (RG1) and the second recognition site is located between sequence (ii) and sequence (iii),
(b) introducing the target vector in a host cell under conditions in order to allow random integration of the target vector into the genome of the host cell, and
(c) selecting a host cell having stably integrated the target vector and showing transcriptional activity of the RG1.

A further aspect of the present invention is a method for the production of recombinant gene products, comprising the steps
(a) providing a wildcard host cell having integrated in its genome an expression cassette comprising
(i) a reporter gene (RG1) operatively linked to a first expression control sequence (P1),
(ii) a first selection marker gene (SM1) operatively linked to a second expression control sequence (P2),
(iii) a second non-functional selection marker gene (SM2) without operative linkage to an expression control sequence,
wherein sequence (i) is located in the 5'-position, sequence (ii) is located between (i) and (iii) and sequence (iii) is located in the 3'-position,
(iv) a first and a second recognition site for a double-strand break mediating enzyme, wherein the first recognition site is located between the first expression control sequence (P1) and the first reporter gene (RG1) and the second recognition site is located between sequence (ii) and sequence (iii),
wherein the expression cassette is stably integrated in the host cell genome and shows transcriptional activity of the reporter gene (RG1),
(b) providing an exchange vector comprising:
a gene of interest (GOI), and
an inactive second selection marker gene (ΔSM2) operatively linked to a third expression control sequence (P3),
wherein the exchange vector comprises a first 5'-homologous sequence and a second 3'-homologous sequence, which allow recombination with sequences of the target vector,
(c) introducing the exchange vector into a host cell obtained in step (c) under conditions to allow a double strand break at the first and/or second recognition site, preferably at the first and second recognition site, as defined in (a)(iv) and an integration of the exchange vector into the genome of the host cell by double-strand break-mediated homologous recombination,
whereby the inactive second selection marker gene (ΔSM2) is activated by an integration of the exchange vector,
(d) selecting a producer cell having integrated the exchange vector by homologous recombination with the integrated target vector, wherein the producer cell expresses the GOI.

A further aspect of the present invention is a method for the generation of a producer host cell for the production of recombinant gene products comprising the steps
(a) introducing a nucleic acid sequence comprising a first and a second recognition site for a double-strand break mediating enzyme by targeted homologous recombination into a site of the genome of a host cell which supports transcriptional activity,
(b) selecting a wildcard host cell having stably integrated the first and the second recognition site,
(c) providing an exchange vector comprising
(i) a gene of interest (GOI) and
(ii) a first 5'-homologous sequence and a second 3'-homologous sequence, which allow recombination with sequences at the integration site of the first and/or second integration site,
(d) introducing the exchange vector into a host cell obtained in step (b) under conditions to allow a double-strand break at the first and/or second recognition site defined in (a) and an integration of the exchange vector into the genome of the host cell by double-strand break mediated homologous recombination and (e) selecting a producer cell having integrated the exchange vector by homologous recombination, wherein the producer cell expresses the GOI.

A further aspect of the present invention is a method for the production of a wildcard host cell for the introduction of a gene of interest (GOI), comprising the steps:
(a) introducing a nucleic acid sequence comprising a first and a second recognition site for a double-strand break mediating enzyme by targeted homologous recombination into a site of the genome of a host cell which supports transcriptional activity,
(b) selecting a wildcard host cell having stably integrated the first and the second recognition site.

A further aspect of the present invention is a method for the production of recombinant gene products:
(a) providing a wildcard host cell having integrated in its genome a nucleic acid sequence comprising a first and a second recognition site for a double-strand break mediating enzyme,
  wherein the nucleic acid sequence is stably integrated in the host cell genome at a site which supports transcriptional activity,
(b) providing an exchange vector comprising
  (i) a gene of interest (GOI) and
  (ii) a first 5'-homologous sequence and a second 3'-homologous sequence, which allow recombination with sequences at the integration site of the first and/or second integration site,
(c) introducing the exchange vector into a host cell provided in step (a) under conditions to allow a double-strand break at the first and/or second recognition site defined in (a) and an integration of the exchange vector into the genome of the host cell by double-strand break mediated homologous recombination and
(d) selecting a producer cell having integrated the exchange vector by homologous recombination, wherein the producer cell expresses the GOI.

A further aspect of the present invention is a target vector comprising
(a) a reporter gene (RG1) operatively linked to a first expression control sequence (P1),
(b) a first selection marker gene (SM1) operatively linked to a second expression control sequence (P2),
(c) a non-functional second selection marker gene (SM2) without operative linkage to an expression control sequence,
  wherein sequence (i) is located in the 5'-position, sequence (ii) is located between (i) and (iii) and sequence (iii) is located in the 3'-position,
  a first and a second recognition site for a double-strand break mediating enzyme, particularly a meganuclease, wherein the first recognition site is located between the first expression control sequence (P1) and the first reporter gene (RG1) and the second recognition site is located between sequence (ii) and sequence (iii).

A further aspect of the present invention is an exchange vector comprising comprising
(i) gene of interest (GOI), and
(ii) an inactive second selection marker gene (ΔSM2) operatively linked to a third expression control sequence (P3),
wherein the exchange vector comprises a first 5'-homologous sequence and a second 3'-homologous sequence, which allow recombination with predetermined sites in the genome of a host cell, e.g. with sequences of the target vector.

Further aspects of the present invention refer to universal wildcard host cells for the introduction and efficient expression of a gene of interest obtainable by the above described methods and high-yield production cells for the large scale production of recombinant gene products produced by using such wildcard host cells using the described methods.

4. DETAILED DESCRIPTION OF THE INVENTION

4.1 Host Cells

The present invention refers to the generation of a producer or wildcard host cell. Preferably the host cell is an eukaryotic cell, e.g. a yeast cell, a fungal cell or a vertebrate cell such as an insect or a mammalian cell. More preferably, the host cell is a mammalian cell, e.g. a rodent cell such as a mouse, rat or hamster cell or a primate cell such as a human cell. In an especially preferred embodiment, the host cell is a Chinese hamster ovary (CHO) cell. Further preferred cells are NSO cells, hybridoma, e.g. mouse or mouse/human cells, HEK 293 cells or Per C6 cells. In a particular embodiment the host cell is capable of growing at high cell densities under serum-free conditions in suspension culture.

4.2 Vector Systems

The present invention involves the use of different vectors, namely a target vector for introducing a reporter gene cassette into a host cell to obtain a wildcard host cell and an exchange or integration vector to introduce a gene of interest (GOI) into a wildcard host cell in order to generate a producer cell. Optionally a third vector for the expression of a double-strand break mediating enzyme in the host cell is used.

The vectors are selected in order to be compatible with the respective host cell. Thus, the vectors are particularly suitable for eukaryotic cells. Preferably, the vectors are non-viral vectors, e.g. circular or linear plasmid vectors.

4.2.1 Target Vector

4.2.1.1 Target Vector for Random Integration

The target vector of the present invention preferably comprises a reporter gene (RG1) and a first selection marker gene (SM1). Both genes preferably form bicistronic expression cassette, wherein the RG1 is operatively linked to a first expression control sequence (P1) and the SM1 gene is operatively linked to a second expression control sequence (P2). The RG1 is preferably located 5' to the SM1 gene. Further, the target vector comprises a non-functional second selection marker gene (SM2). Further, the target vector is preferably substantially free from prokaryotic sequence elements.

The RG1 may be any reporter gene, which expresses a detectable gene product, e.g. an enzyme or a luminescent gene product. Preferably, the reporter gene is a gene the expression of which can be monitored and quantified. Typical examples of reporter genes are alkaline phosphatase, e.g. a secreted alkaline phosphatase (SEAP), luciferase, β-galactosidase or fluorescent proteins such as GFP or variants thereof.

The RG1 is operatively linked to the first expression control sequence (P1), which preferably comprises a constitutive promoter capable of driving the expression of the reporter gene in the host cell. In one embodiment, P1 may comprise a strong constitutive promoter, e.g. a CMV promoter (like the immediate/early promoter with enhancer derived from human or murine CMV virus), which may additionally be enhanced, e.g. by supplementation with the CMV intron A, whereby transcriptional activity and mRNA stability are increased. In general any control sequence allowing a high and constitutive expression in a eukaryotic cell could be used. Those sequences could be naturally-occurring or combinations of naturally-occurring elements. In addition also synthetic promoter-elements may be used. Further examples of suitable first expression control sequences (P1) are the human elongation factor 1 alpha (EF-1 alpha) promoter (with and without the corresponding first intron), promoters derived from Rous sarcoma virus (RSV) LTR, or HIV2 LTR or combinations of sequences derived therefrom.

In a different embodiment, P1 may comprise an attenuated promoter the strength of which is reduced compared to the wildtype promoter, e.g. an alternated CMV promoter. Promoter strength may be reduced, e.g. by modifying the expression enhancing effect of the intron A sequence. This can be done by incorporating short heterologous nucleotide sequences (e.g. up to 100 bp) in the 3'-region of the intron. These insertions do not negatively affect homologous recombination with the exchange vector. By choosing appropriate sequences in the exchange vector, the attenuated version of the promoter may be exchanged by the fully active version when the exchange vector is inserted into the host cell genome.

The first selection marker gene (SM 1) may be any selection marker gene which is capable of providing a selectable phenotype in the host cell. For example, the SM1 may be an antibiotic resistance gene such as a neomycin or hygromycin resistance gene. In addition also selectable markers such as genes conferring resistance to blasticidin, puromycin, ouabain or the glutamine synthase gene could be used.

The SM1 is in operative linkage with a second expression control sequence (P2), which preferably comprises a constitutive promoter, e.g. the SV-40 promoter. In a particular embodiment, P2 may comprise an attenuated promoter, i.e. a promoter which is an attenuated version of the wildtype promoter. Alternatively or additionally, the SM1 may be an attenuated selection marker gene with a reduced activity compared to the wildtype selection marker gene. By using an attenuated promoter and/or selection marker gene, the selection of a host cell having integrated the target vector at an integration site with high transcriptional activity may be facilitated.

In an alternative embodiment, the expression of SM1 is achieved by the use of an IRES element placed between the 3'-end of the RG1 coding sequence and the 5'-end of the SM1 coding sequence.

Further, the target vector typically contains polyadenylation signals at the 3'-end of the coding sequences for RG1 and SM1, e.g. the polyadenylation signals of bovine growth hormone or the SV-40 polyadenylation signal.

The target vector further comprises a second nonfunctional selection marker gene (SM2) without operative linkage to an expression control sequence. The SM2 is located outside, preferably at the 3'-side of the bicistronic expression cassette for RG1 and SM1 . In a particular embodiment, the coding sequence for the SM2 is without ATG start codon and/or an upstream stop codon, preferably with upstream stop codons in all three reading frames.

The SM2 may be any selection marker which is capable of providing a selectable phenotype in the host cell. Preferably, the SM2 is different from the SM1 . For example, the SM2 may an antibiotic resistance gene such as a neomycin or hygromycin resistance gene. Further examples are genes conferring resistance to blasticidin, puromycin, ouabain or the glutamine synthase gene.

In order to induce specific double-strand breaks within the target vector, it comprises a first and a second recognition site for a double-strand break mediating enzyme, particularly a meganuclease. The first recognition site is located between P1 and the coding sequence of RG1 and the second recognition site is located between the coding sequence for SM1 and the nonfunctional sequence SM2 . The part of the target vector flanked by two recognition sites may be designated as exchange-area.

In a particular embodiment, the second recognition site may be located between the stop codon of SM1 and the following polyadenylation signal (target vector A). In a further embodiment, the second recognition site may be located between the SM1 polyadenylation signal and the start of the coding sequence of SM2 (target vector B).

The two recognition sites may have the same orientation or an opposite orientation relative to each other. In a preferred embodiment, the part of the recognition site corresponding to the downstream exon of the wildtype site is located outside the exchange area after cutting.

The double-strand break mediating enzyme is preferably a meganuclease or homing nuclease, which has a recognition site rarely occurring in the host cell genome, for example a group I intron encoded homing nuclease. Preferably, the meganuclease or homing nuclease has a recognition site, which does not naturally occur within the host cell genome. The recognition site has typically a length of at least 10 and preferably of at least 12 nucleotides. More preferably, the nuclease has a recognition site of 18 nucleotides, thus belonging to the dodecapeptide family of endonucleases. Examples of such enzymes are described in US 2005/0032223, the content of which is herein incorporated by reference. Preferably, the meganuclease is selected from I-SceI, I-SceII, I-SceIll, I-SceIV, I-CeuI, I-CreI, I-PpoI, I-TevI, I-TevII, I-TevIII, HO and Endo SceI. More preferably, the meganuclease is I-SceI.

Two embodiments of the target vector of the invention are shown in FIGS. 1 (target vector A) and 2 (target vector B). The reporter gene is operatively linked to the enhanced CMV promoter (eCMV) including intron A. The first selection marker gene (SM1) is operatively linked to an SV40 promoter (Psv40). The second selection marker gene (SM2) is not operatively linked to a promoter and thus non-functional.

4.2.1.2 Target Vector for Non-Random Integration

In a different embodiment of the invention, the target vector may additionally comprise a first 5'- and a second 3'-homologous sequence, which flank the genetic elements of the target vector as described above and allow non-random homologous recombination at a predetermined gene locus of the host cell, i.e. a gene locus known to support transcriptional activity, e.g. an immunoglobulin locus. In this embodiment the reporter gene may be operatively linked to an expression control sequence as described above or alternatively lack an expression control sequence if the flanking homologous sequences are selected to allow homologous recombination at a position which places the reporter gene (RG1) in operative linkage with an endogenous expression control sequence.

Alternatively, a target vector lacking a reporter gene may be used for this embodiment.

4.2.2 The Exchange Vector

The exchange vector preferably comprises a gene of interest (GOI) and an inactive, e.g. incomplete coding sequence for a second selection marker gene (ΔSM2). The gene of interest may be any gene encoding a desired gene product, particularly a recombinant protein, but also a recombinant nucleic acid, e.g. a desired RNA molecule. Preferably, the GOI is present without a functional expression control sequence. More preferably, the GOI contains at its 5'-end a partial expression control sequence, which is identical or substantially identical to the 3'-prime part of the first expression control sequence (P1) in the target vector. Further, it is preferred that an appropriate polyadenylation signal for the GOI is located at the 3'-end of the coding sequence as described for the target vector.

The inactive coding sequence for SM2 does not allow the generation of a functional selection marker. For this purpose, typically the 3' portion of the coding sequence of SM2 may be lacking in the exchange vector. The inactive coding sequence for SM2 is, however, in operative linkage to a functional expression control sequence, e.g. a constitutive promoter such as the SV40 promoter.

In a further embodiment, the exchange vector additionally comprises a third selection marker gene (SM3), which is cotranscribed with the GOI. For this purpose, the coding sequence for SM3 operatively linked to an IRES element may be placed between the 3'-end of the coding sequence for the GOI and the polyadenylation site. Alternatively, the order of the GOI and SM3 may be exchanged. In a further embodiment the GOI and SM3 are expressed from independent expression cassettes with separate expression control elements (promoters). The SM3 is different from SM2 and allows the selection of cells independent from SM2. Thus, a double selection allows the enrichment of cells expressing both selection markers. Both selection markers may be selected, without limitation, from genes conferring resistance to hygromycin, neomycin, G418, blasticidin, puromycin, ouabain or the glutamine synthase gene.

The length of the partial promoter sequence 5' of the GOI and the length of the incomplete SM2 is chosen in a way that efficient homologous recombination is possible between the respective homologous elements on the target vector.

Further, the exchange vector comprises a first 5'-homologous sequence and a second 3'-homologous sequence, which allow recombination with sequences of the target vector. The length of the respective homologous sequences is preferably at least about 500 nucleotides, more preferably at least about 700 nucleotides. In an especially preferred embodiment, the 5'-homologous sequence has a length of at least about 1000 nucleotides and the 3'-homologous sequence has a length of at least about 700 nucleotides.

The maximum length of the homologous sequences is preferably about 2000 nucleotides. The degree of identity between the homologous sequences on the target and exchange vector is preferably at least 80%, more preferably at least 90% over the total sequence. Most preferably, the homologous sequences are substantially identical in order to obtain a maximum exchange rate. Further it is preferred that the 5'-homologous sequence in the exchange vector does not comprise a functional promoter. The 3'-homologous sequence in the exchange vector does preferably not comprise a functional selection marker sequence.

Additionally, the exchange vector may comprise a fourth selection marker gene outside the sequence region defined by the first 5'- and second 3'-homologous sequence. The fourth selection marker gene is a negative selection marker gene, e.g. a suicide gene such as HSV-thymidine kinase, which allows selection against any random integration of the exchange vector into the host cell genome by which the negative selection marker is also integrated.

Figure 3:
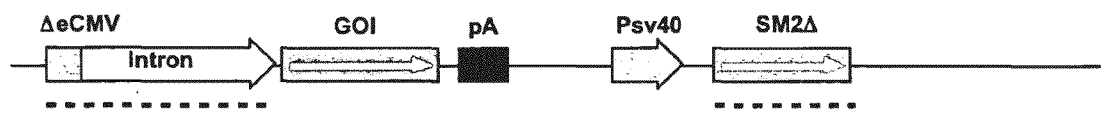
Figure 4:
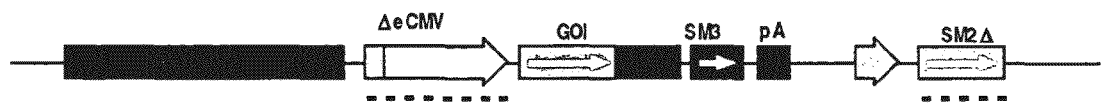

Two embodiments of the exchange vector are shown in FIG. 3 (exchange vector A) and FIG. 4 (exchange vector B). The gene of interest (GOI) is operatively linked to the 5'-deleted partial eCMV promoter (ΔCMV). The second selection marker (SM2) is operatively linked to the SV40 promoter (Psv40). The homologous sequences with the target vector are indicated by dotted lines. The exchange vector B (FIG. 4) additionally comprises a suicide gene (HSV-tk) outside the homologous sequences and a third selection marker co-transmitted with the GOI gene (SM3) operatively linked to an IRES element.

In an alternative embodiment, the exchange vector may comprise an active second selection marker gene (SM2) operatively linked to an expression control sequence instead of the inactive second selection marker gene.

4.3 Generation of Wildcard Cell Lines 4.3.1 Random Integration

In order to generate a wildcard host cell, a target vector as described above is under Section 4.2.1.1 may be introduced into a host cell under conditions in order to allow random integration of the target vector into the genome of the host cell by non-homologous, i.e. random recombination.

In a particular embodiment the target vector has been deprived from un-needed bacterial elements prior to transfection. This will eliminate a gene silencing effect mediated by bacterial DNA elements.

Conditions for transfection are chosen in a way that preferentially only a single integration site is tagged. In addition the integration of a single copy of the target vector is favored.

The selection of stably transfected host cells is facilitated by use of the SM1, which is typically an antibiotic resistance gene such as a neomycin or hygromycin resistance gene. Thus, the selection procedure preferably comprises a growth of the transfected cells in the presence of an antibiotic against which SM1 mediates resistance.

In a next step, a host cell having integrated the target vector and exhibiting a high expression of the reporter gene (RG1) is selected. Preferably, a clonal to oligo-clonal cell population is generated for this purpose by a limited dilution strategy. Preferably, this step is performed under serum-free culture conditions using host cells adapted to growth in suspension.

In a preferred embodiment of this selection procedure, transfected cells are seeded at a density that will result after selection in a cell population that is preferentially derived from 1-5 cells. Clonal or oligo-clonal cell populations will be expanded and the transcriptional capacity of the random tagged genomic locus is analyzed by the reporter gene (RG1). Preferably, a quantitative analysis of the RG1 expression is carried out.

Based on the expressed levels of RG1 high producing clones are selected. In order to derive a single-cell derived host-cell population as potential wildcard cell lines a second limited dilution cloning is preferably performed. In a further preferred step, the cells are selected according to their growth properties, particularly preferred cells exhibit a fast growth rate corresponding to a low doubling-time, particularly under serum-free culture conditions.

In a preferred embodiment, the selection procedure may involve the following steps:
(i) Selecting from the host-cells with integrated target vector those, with high and stable expression of the reporter gene (RG1);
(ii) Selecting from the cells obtained under (i) those which phenotype allows the efficient large scale cultivation under industrial culture conditions (i.e. dynamic culture systems like spinners, stirred tanks, wave-reactors, fluidized-bed reactors or fixed-bed reactors); and
(iii) Selecting from the cells obtained under (ii) those which allow the efficient exchange of the reporter-cassette against an expression cassette for a gene of interest.

The selection of an appropriate "wildcard"-cell line with sufficient production capacity can be performed by screening for the activity of a secreted reporter like the human placental secreted alkaline phosphatase (hSEAP) or an appropriate other quantifiable reporter protein. In order to derive a single-cell derived host-cell population as a potential wildcard-cell line a second limited dilution cloning is preferably performed.

In a further embodiment the selection of a high-expressing wildcard host cell may also be performed using a fluorescent protein like the green fluorescent protein (GFP) or variants, i.e. red fluorescent protein (RFP), blue fluorescent protein (BFP), cyan fluorescent protein (CFP), yellow fluorescent protein (YFP) or further variants. By means of the expressed reporter the cells with high expression can be enriched from a pool of transfected cells by fluorescent activated cell sorting (FACS) or after appropriate labeling by magnetic enrichment (MACS or similar techniques). By several subsequent enrichment cycles a population with high-expression for the respective reporter can be obtained. The final wildcard cell is preferably also generated by limited dilution cloning of these enriched polyclonal cell population.

Further preferred examples of reporter genes are chloramphenicol transferase, β-galactosidase, β-glucuronidase, luciferase etc.

In an especially preferred embodiment, an "outperformer" wildcard cell line is selected, which has a reporter gene expression level, which is preferably at least 10-fold, more preferably at least 20-fold and still more preferably at least 25-fold compared to the average expression levels of the resulting population of clones.

In a further preferred embodiment, at least 1000, e.g. at least 2000 or at least 3000 primary clonal or oligoclonal cell populations are analyzed in order to identify high-expressing wildcard host cell lines, e.g. outperformer wildcard host cell lines.

The preferred wildcard cell lines have integrated a single copy of the target vector in a highly transcriptional active site. For the selection of appropriate wildcard cells the number of integration sites and the number of integrated copies of target vectors will preferentially be taken into account. Analysis of the number of integrated target vectors and number of integration site could be done by PCR—(preferentially by real-time quantitative PCR) and Southern blot analysis or in situ hybridization.

In a further embodiment the final wildcard host-cell might harbor in addition to the stable integrated target vector an expression cassette for the double strand break (DSB) mediating enzyme used during the exchange reaction. This expression cassette could be part of the target vector or introduced as a separate vector. This expression cassette contains preferentially an inducible promoter in order to reach a timely controlled expression of the DSB-mediating enzyme.

4.3.2 Non-Random Integration

In a different embodiment, the first and second recognition sites for the DSB mediating enzyme may be introduced by targeted homologous recombination to a predetermined site of the host cell genome, which is known to support transcriptional activity, e.g. the immunoglobulin locus. For this purpose, preferably a target vector for non-random integration as described in Section 4.2.1.2 is used. A selection procedure may be carried out described in Section 4.3.1.

It should be noted, however, that a selection procedure may not be required in some variants of this embodiment since the recognition sites are introduced at a predetermined site known to support transcriptional activity.

4.4 Exchange of Expression Cassettes within Wildcard Cells

For an exchange of the expression cassette, an exchange vector as described above is introduced into a wildcard host cell, i.e. a wildcard host cell obtained by random or non-random integration of the target vector into the host cell genome, under conditions to allow a double-strand break at the first and/or second recognition site present on the target vector. Thereby, an integration of the exchange vector into the genome of the host cell by double-strand break mediated homologous recombination is achieved.

For this purpose, the wildcard host cell is preferably co-transfected with the exchange vector as described above and a further vector expressing the meganuclease, particularly a homing endonuclease (HE) compatible with the recognition sites present in the target vector, e.g. I-SceI. Alternatively, the double-strand break mediating enzyme may be expressed in the host cell after transfection with an appropriate mRNA coding for the desired enzyme or by direct delivery of the enzyme to the cell.

The enzyme will cut the recognition site(s) within the target vector. Depending on the number of cut sites, this will simply open the target vector integrated into the genome (one recognition site) or release the exchangeable expression cassette from the target vector (two recognition sites flanking the expression cassette). In both cases the activity of the HE will lead to the generation of a double strand break (DSB) within the genome of the wildcard cell at the defined positions within the target vector.

This DSB will induce homologous recombination (HR) with a frequency that is 100-1000-fold higher than observed for endogenous HR. Within this repair process the transfected exchange vector serves as repair matrix, due to its homologous sequence stretches flanking the expression cassettes.

As result the complete expression cassette with RG1 and SM1 will be removed from the genome of the wildcard cell and substituted by the expression cassette comprising the GOI and in a particular embodiment in addition the SM3, e.g. coupled via an IRES element to the GOI.

The SM3 allows the additional selection of cells that transcribe the expression cassette with GOI and SM3 without the need for analyzing the expression of the GOI.

A further important result of the HR is the activation of the promoterless SM2 in the target vector. Due to the HR with the exchange vector the SM 2 will be supplemented with a promoter and thus facilitates the expression of SM2 within the successful repaired wildcard cell.

Since the promoter is operatively linked only to a truncated version ΔSM2 in the exchange vector, it does not deliver resistance to the cell. After homologous recombination SM2 is activated and allows the efficient selection of cells which have successfully repaired the double strand break by introducing the expression cassette from the exchange vector.

Since this single (using SM2) or double selection (using SM2 and SM3) a homogenous producer cell population with high expression levels for the GOI can be generated without the need of excessive screening.

Since the genomic modification of the wildcard cell is limited to the exchange of the expression cassette at the tagged locus, the phenotype of the cell will not be affected.

Even in cases where a single cell derived cell population is required, this can be obtained within short time, since a limited dilution of the population obtained after the selection is easily done with a high rate of success.

Thus, the present invention provides a fast and reproducible way to generate producer host cells for obtaining desired recombinant gene products, e.g. recombinant proteins or nucleic acids, in large amounts.

Figure 5:
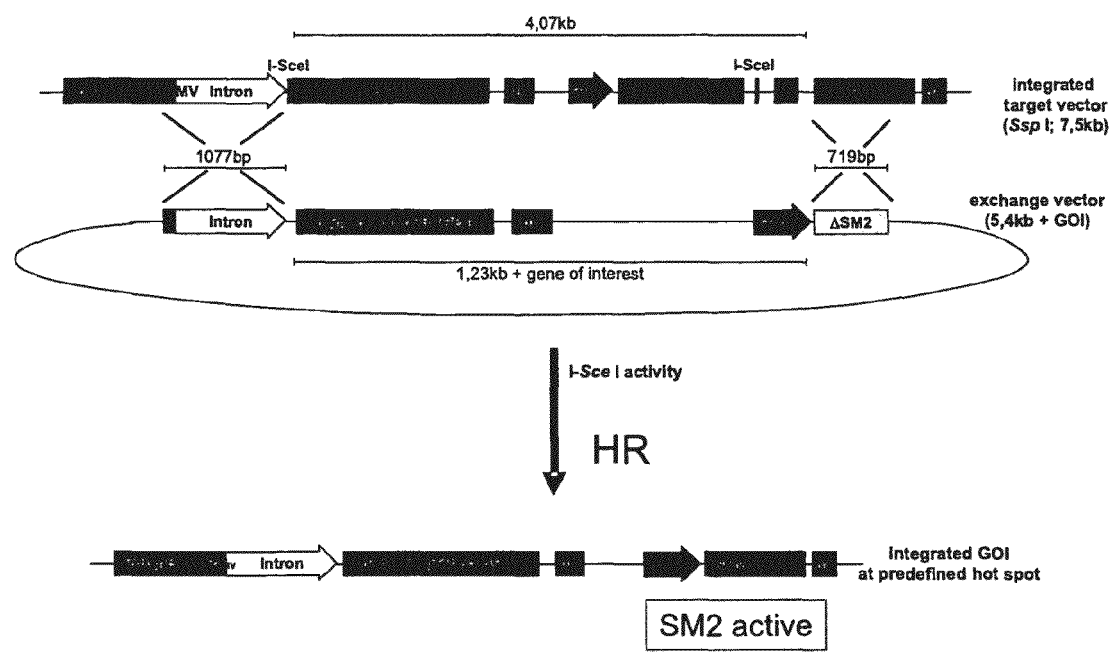
Figure 6:
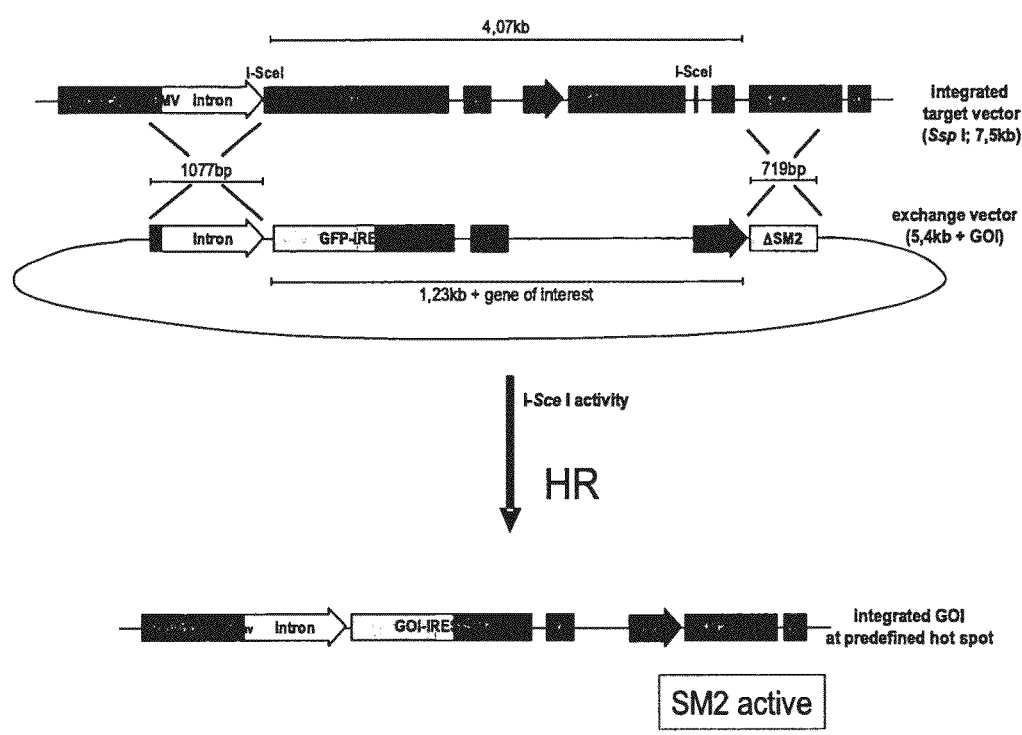

Two schemes of an exchange reaction between the target and exchange vector by homologous recombination are shown in FIGS. 5 and 6.

In a different embodiment, an exchange vector may be introduced into the genome of a wildcard host cell, which is obtained by non-random integration of a first and/or second DSB mediating enzyme recognition site at a predetermined locus of its genome, preferably by using a target vector as described in Section 4.2.1.2 . In this embodiment, the exchange vector preferably comprises (i) a gene of interest (GOI) and
(ii) a first 5'-homologous sequence and a second 3'-homologous sequence, which allow recombination with sequences at the integration site of the first and/or second integration site.

More preferably, an exchange vector is used as described in Section 4.2.2.

Further, the present invention shall be explained in more detail by the following figures and examples.

FIGURES

FIG. 1 Schematic Representation of Genetic Elements in an Embodiment of the Target Vector (Target Vector A)

The target vector contains an exchange cassette with a CMV-promoter (P1) driven reporter gene (RG1) and a first selection marker (SM1) driven by PSV40 (P2) for selection of stable integration of the vector in the genome of a host cell. The exchange cassette is flanked by two recognition sites for a homing endonuclease (I-SceI). The second selection marker (SM2) outside the exchange cassette is without a promoter and thus non-functional in the target vector.

Figure 2:
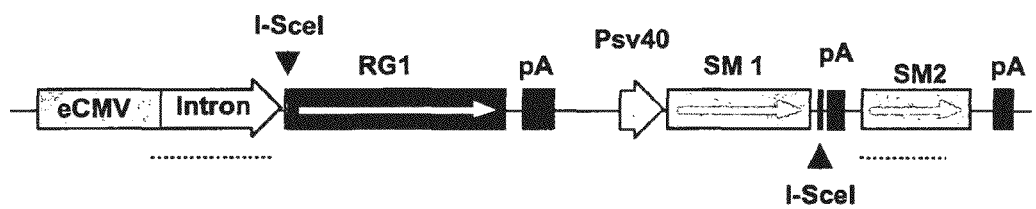

FIG. 2 Schematic Representation of Genetic Elements in a Further Embodiment of the Target Vector (Target Vector B)

In the modified version of the target vector the 3'-I-SceI site is placed before the poly-A signal (pA) of the first selection marker (SM1). In case of religation (endjoining instead of homologous recombination) of the I-SceI cut target vector, the pA-element serves as isolator, preventing the transcription of SM2 . In addition stop-codons are placed in front of the promotorless selection marker 2 (SM2) in order to terminate translation of transcripts not terminated by the pA-element.

FIG. 3 Schematic Representation of Genetic Elements in an Embodiment of the Exchange Vector (Exchange Vector A)

The exchange vector contains a CDS for a GOI and an incomplete CDS for selection marker ($\Delta$SM2). Only the CDS for the GOI is followed by an appropriate polyadenylation signal. While the incomplete CDS for SM2 is driven by a functional constitutive promoter P3 (PSV40), the GOI contains at its 5'-end only a partial promoter which is identical to the 3'-part of the CMV-promoter in the target construct.

FIG. 4 Schematic Representation of Genetic Elements in a Further Embodiment of the Exchange Vector (Exchange Vector B)

In this embodiment the exchange vector contains in addition to the vector depicted in FIG. 3 a third selection marker (SM3) which expression is coupled to the expression of the GOI via an IRES-element. This allows the isolation of cells with successful exchanged expression cassettes by a double-selection using selection marker 2 and 3.

To be able to eliminate cells which have integrated the complete exchange vector randomly into their genome the exchange vector contains in this embodiment an HSV-TK-gene as a suicide gene.

FIG. 5 Scheme of Exchange Reaction Between Target and Exchange Vector by Homologous Recombination (HR)

The target vector at the tagged genomic locus with reporter (RG1) and selection cassette (SM1) is flanked by homing endonuclease recognition sites (I-SceI). The promoter P1 is represented by the "enhancer-PCMV-Intron" element. Promoter P2 is represented by the SV40-promoter (PSV40). The exchange vector harbours the GOI and a nonfunctional selection marker ($\Delta$SM2). Regions of homology used for repair of the homing-endonuclease mediated DSBs by homologous recombination (HR) are depicted. The promoter P3 in the exchange vector is represented by a SV40-promoter (PSV40).

The lower part shows a tagged genomic locus after successful exchange of expression cassettes.

FIG. 6 Scheme of Modified Exchange Reaction using a Third Selection Marker (SM3)

The exchange reaction is performed as described in FIG. 5 between the target vector at a tagged genomic locus and the exchange vector. Within this embodiment, the exchange vector contains in addition to the GOI a third selection marker (SM3) the expression of which is coupled to the GOI via an IRES-element.

Figure 7:
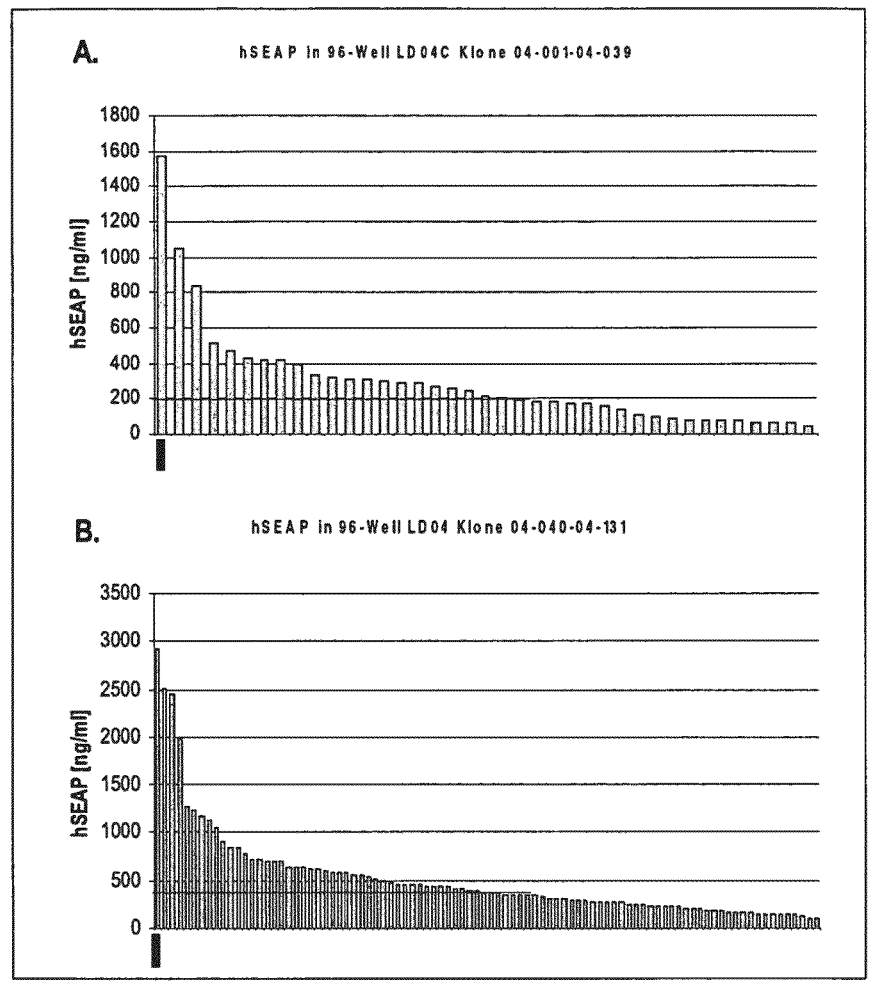

FIG. 7 Measurement of hSEAP Activities in Panels of Primary Cell Clones

The individual clonal or oligoclonal cell populations (x-axis) are selected based on the activity of SM1 for stable integration of the target vector. Cells were expanded and screened for the transcriptional activity of the random tagged integration locus based on the activity of the RG1 (hSEAP). Activity of the reporter hSEAP is given in ng/ml at the y-axis. A. Distribution of hSEAP-activity in 39 individual cell populations. B. Distribution of hSEAP-activity in 92 individual cell populations.

Figure 8:
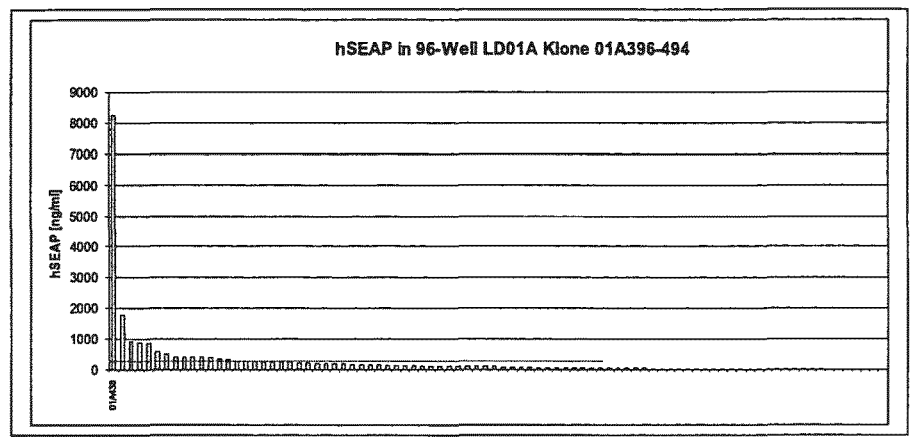

FIG. 8 Primary Screening of Potential Universal Host Cells

Cell populations are generated as described in FIG. 7 by selection of cells using SM1 after transfection with the target vector. The data demonstrate the identification of a desired high-producer cell population termed "outperformer". Identification is based on the expression of the RG1 (hSEAP). Activity of the reporter hSEAP is given in ng/ml at the y-axis.

Figure 9:
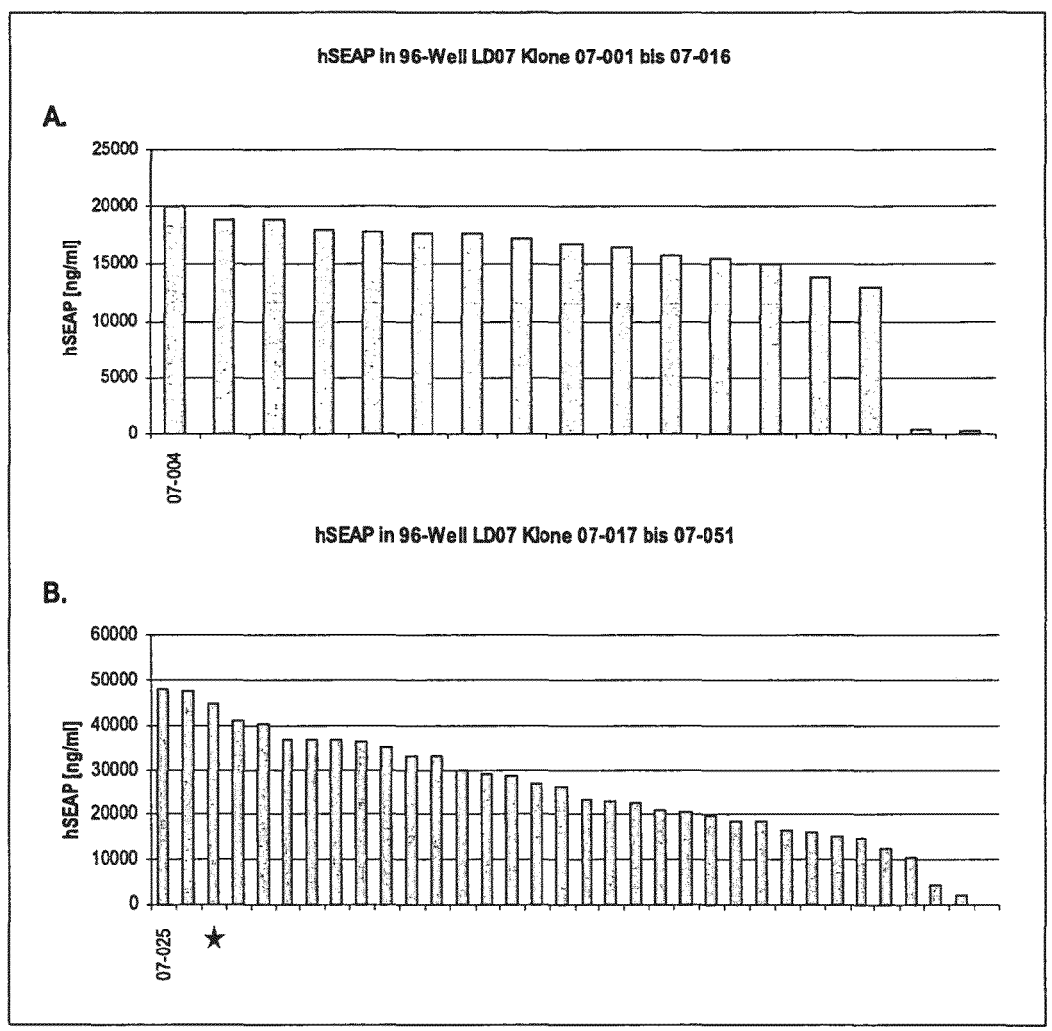

FIG. 9 Secondary Screening of Outperformer 01A438

From outperformer cells, characterized by high expression of the RG1 (hSEAP), high-expressing, clonal cell populations are generated by limited dilution (LD) cloning of single cells under serum-free conditions. Graphs A. and B. depict the different expression capacity of individual clonal cells populations as demonstrated by the activity of the RG1 (hSEAP). Activity of the reporter hSEAP is given in ng/ml at the y-axis. The asterisk in B. denotes a cell clone selected as wildcard-cell (denoted 07-022) for further use. Selection was based on expression and growth characteristics.

Figure 10:
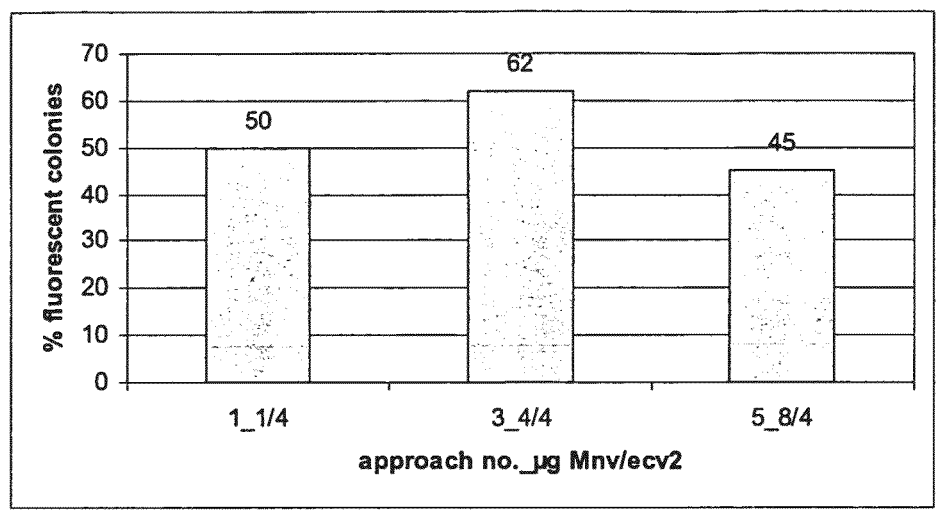

FIG. 10 Double-Strand Break Mediated Exchange: Optimization of Meganuclease Plasmid Amount Exchange of expression cassettes in a preformed wildcard cell 07-022 with stable integrated target vector. The expression cassette from the tagged wildcard cells was exchanged against a GFP-IRES-SM3 cassette with GFP as model GOI by means of DSB-mediated HR between the target vector and the exchange vector. The exchange was performed by co-transfection of the exchange vector (ecv2) and an expression vector for the meganuclease (Mnv). In order to optimize the exchange reaction a constant amount of exchange vector was tested with different amounts of meganuclease plasmid. Successful exchange of the expression cassettes by homologous recombination between the target- and the exchange vector will activate the SM2 (NeoR). After selection of $2\times10^6$ with G418 for 11 days the total number of G418-resistant colonies, as well as the amount of GFP-positive colonies was determined. The graph depicts the percentage of GFP-positive cells in the different approaches. Note that approach 5 yielded approx. 6-fold more GFP-expressing clonal cells than approach 3.

Figure 11:
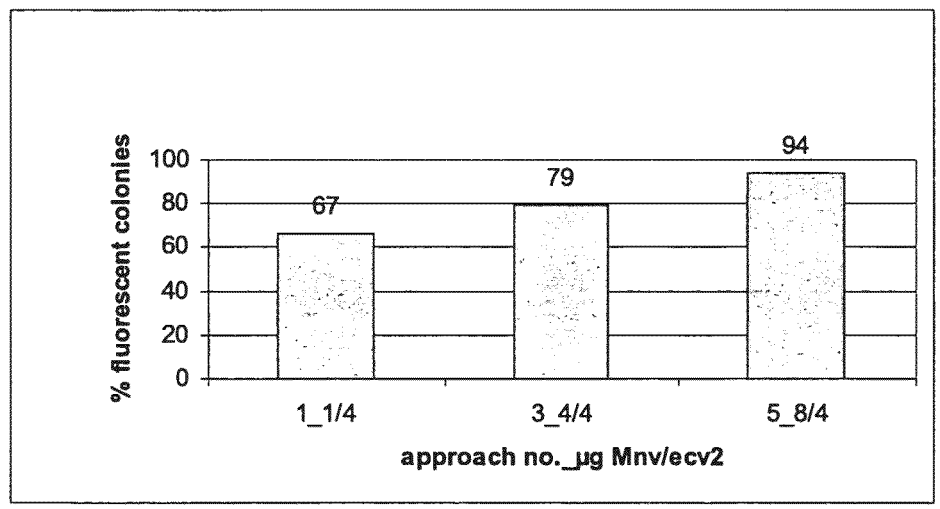

FIG. 11 Double-Strand Break Mediated Exchange: Optimization of Meganuclease Plasmid Amount Cells from the approach described for FIG. 10 are further selected using the activity of SM3 (ZeoR) in in addition to SM2. After double selection the total number of double-resistant colonies, as well as the amount of GFP-positive colonies among them was determined by UV-microscopy. Approach 5 shows the highest percentage (~94%) and with 261 clones the highest absolute number of double-resistant and bright GFP-expressing cells.

Figure 12:
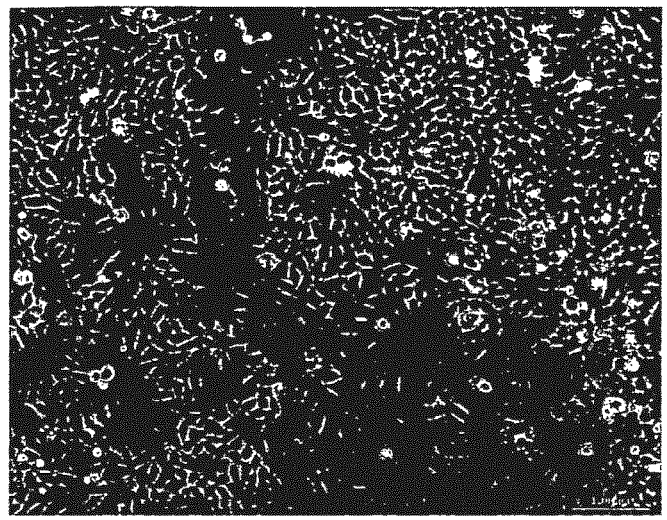

FIG. 12 Double-Strand Break Mediated Exchange: Optimization of Meganuclease Plasmid Amount Example of clonal cells obtained by exchange of expression cassettes in wildcard-cells by double strand break (DSB)-induced homologous recombination between the target vector and the exchange vector. The picture shows an overlay (visible/UV-light) of a GFP-positive colony from approach 5 described in FIGS. 10 and 11. Scale-bar indicates 100 μm.

Figure 13:
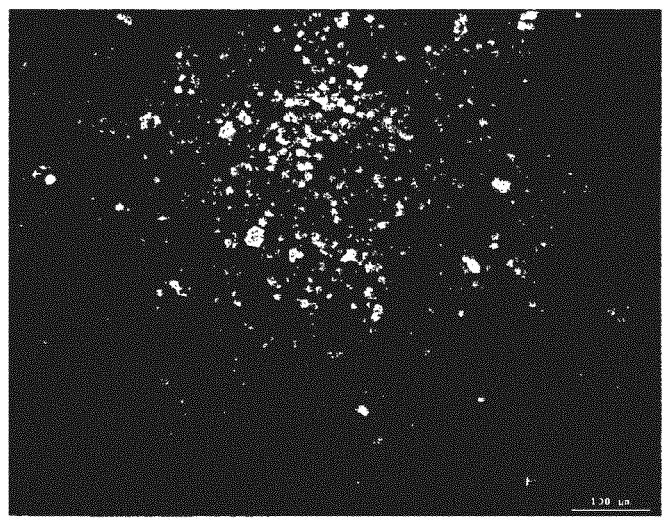

FIG. 13 GFP-Positive Colony Derived from Wildcard-Cell Clone 01C090

Example of a successful cassette-exchange by the described method using a different wildcard-cell population (01C090). The picture shows GFP-expressing cells obtained after cassette exchange and double selection based on SM2 and SM3. Scale-bar indicates 100 μm.

Figure 14:
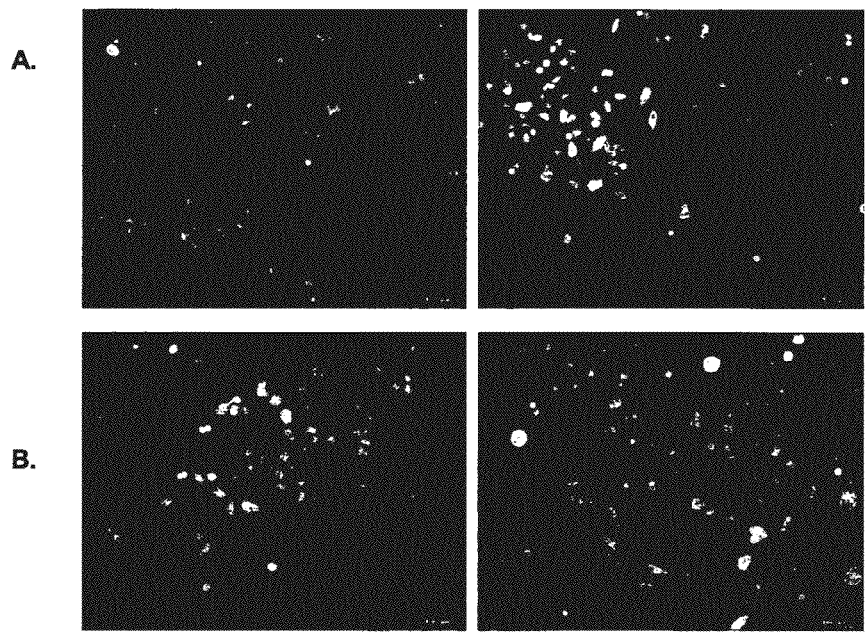

FIG. 14 GFP-Positive Colonies After Exchange Reaction and Double Selection

Further examples of successful cassette exchange by DSB-mediated exchange of expression cassettes in established wildcard-cell clones. Cells obtained after exchange and double selection from wildcard-cell clone 07-022 (A) and clone 08-018 (B) are shown in comparison. Scale-bar indicates 100 μm.

Figure 15:
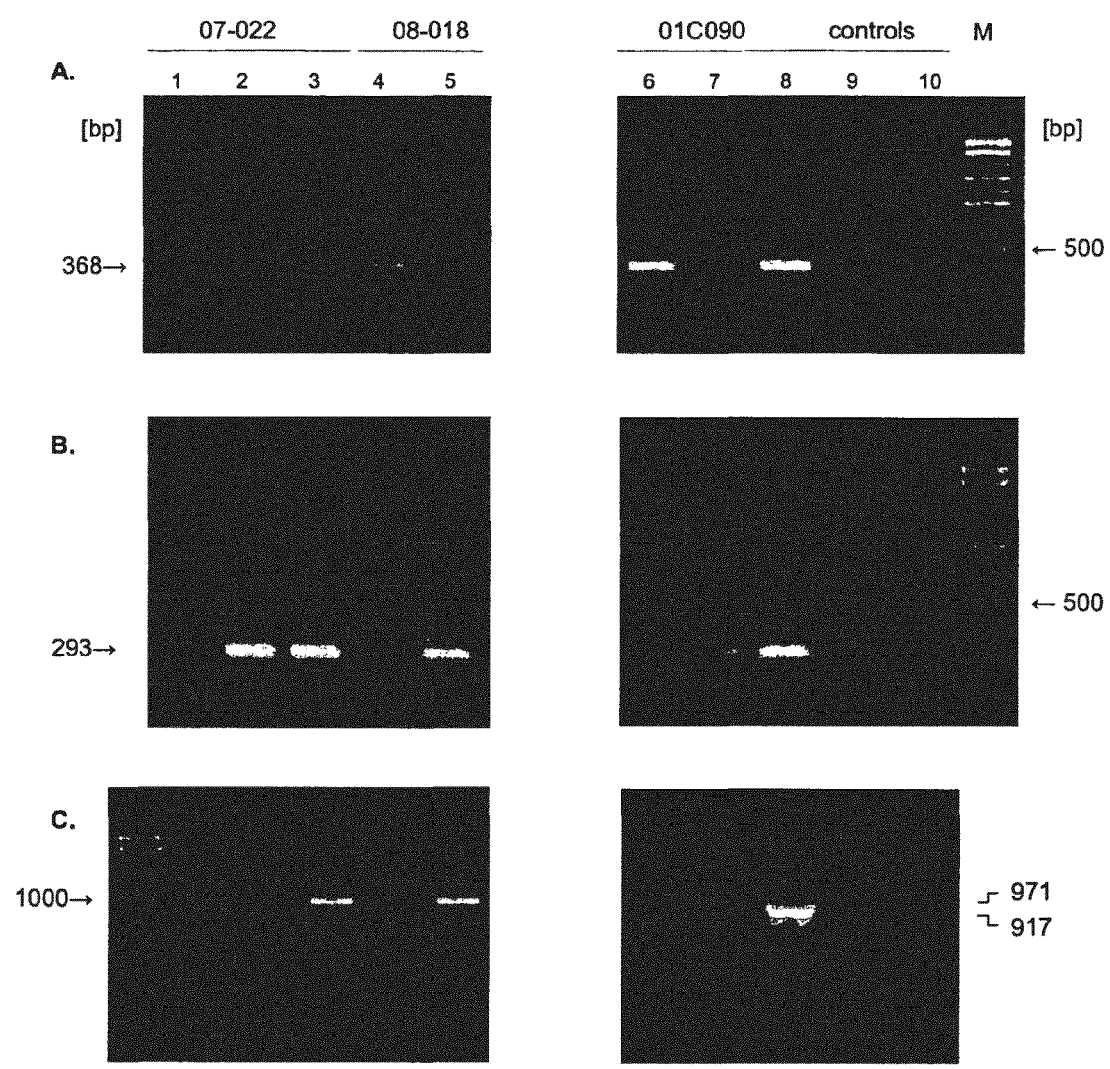

FIG. 15 PCR-Based Confirmation of Exchange Reaction

Genomic DNA from three different wildcard clones (07-022, 08-018, 01C090) was analyzed by PCR before (lane 1, 4, 6) and after the exchange reaction (lane 3, 5, 7). For 07-022 also a control with random integrated exchange vector was analyzed (lane 2). (A.) A 368 bp product confirms the presence of the hSEAP-expression cassette prior the exchange (lanes 1, 4, 6). The missing band after the exchange (lane 3, 5, 7) indicates the complete removal of this expression cassette. (B.) A 293 bp product confirms the presence of the GFP-expression cassette after the exchange reaction (lane 3, 5, 7), but also after random integration (lane 2). (C.) A 971 bp product is only generated after completion of SM2 and thus indicates the exchange of expression cassettes by HR (lane 3, 5, 7). Appropriate plasmids served as positive controls (lane 8). Note that control in (C) shows a 917 by band due to the used plasmid DNA. Negative controls contained instead of template DNA water (lane 9) or genomic DNA from parental control cells without any modifications (lane 10) Data were compiled from different agarose gels.

5. EXAMPLES

5.1 Generation of the Vector System

5.1.1 Generation of a Target Vector

The original CMV-promoter from vector pcDNA3.1(+) was removed by restriction with NheI and NruI. The extended CMV-promoter with the intron A was removed from vector pMG with PacI and after blunting with XbaI. This 1.7 kb long fragment was ligated into the NruI and NheI (compatible with XbaI) cut pcDNA3.1 fragment. Thereby vector CV001 was generated.

The 5' I-SceI site was introduced into CV001 by an adaptor strategy. Complementary oligonucleotides with the I-SceI site TAGGGATAACAGGGTAAT and HindIII overhanging ends were hybridized and cloned into the HindIII of CV001 resulting in CV001-MN.

The original neomycin resistance (NeoR) gene of the pcDNA3.1 (+) in CV001-MN was replaced by a hygromycin resistance (HygroR) gene as SM1. To this end the HygroR gene including an polyA-site was amplified from a plasmid in a way that the HygroR-CDS was missing the first 4 nt (including the start ATG) from the 5'-end and contains at its 3'-end a PciI restriction site. After digestion with PciI the PCR-product was ligated into the non-methylated CV001-MN restricted with BsaBI and PciI. By cloning into the the BsaBI site the HygroR-CDS was completed by adding the missing ATGA to the 5'-end from the vector. In the resulting vector CV001-MN-Hygro a promotorless NeoR gene was introduced as SM2. To this end a complete NeoR-CDS was amplified by PCR from an appropriate plasmid DNA. The 5'-primer was used to introduce an I-SceI site and further allows cloning of the NeoR-CDS by PciI. The 3'-primer introduces a BstZ17I (TAC) site.

After restriction with PciI and BstZ17I the PCR-fragment was gel purified and ligated into the vector CV001-MN-Hygro cut with the same restriction enzymes.

To finalize the target vector the obtained vector CV001-MN2-Hygro-Neo was supplemented with a secreted alkaline phosphatase (hSEAP)-gene as RG1. The hSEAP-CDS including poly-A signal was removed from an appropriate vector by KpnI and XbaI digestion. The fragment was cloned into the KpnI and XbaI site of vector CV001-MN2-Hygro-Neo. The final target vector was termed pCTV-SAP-Hyg-01.

5.1.2 Generation of an Exchange Vector

Based on the vector CV001 the exchange vector B according to FIG. 4 was generated. In order to generate a non-functional truncated version of SM2 the NeoR-CDS from CV001 was removed by BstZ17I and BlnI digestion. The NeoR-CDS was replaced by a 631 by BlnI-NaeI NeoR-fragment. This truncated NeoR-gene is missing the sequence coding for the 24 amino acids of the C-terminal part of the enzyme, which are crucial for its function.

In the resulting CV001-ΔNeoR vector the 5'-region of the CMV promoter, containing the enhancer and the RNA-polymerase II promoter, was removed by double digestion with BsmBI and MunI. This left mainly the intron A sequence from the CMV-intron A promoter element in CV001. After filling up the recessed 3'-ends with Klenow enzyme the vector was closed by blunt-end relegation.

The resulting vector CV001-InA-ΔNeoR is ready for introduction of a free selectable GOI and serves as general exchange vector. As example for a GOI the green fluorescence protein (GFP) was chosen. In this particular case the expression of GFP was coupled to the expression of a third selection marker (SM3) via an IRES element. As SM3 the Zeocine resistance gene (ZeoR) has been chosen. The expression cassette consisting of the sequence for L-GFP followed by an IRES element and the CDS for ZeoR was removed from the vector pMono-Zeo-GFP (Invitrogen) as AgeI-SalI fragment. This cassette has been placed by blunt end ligation into the EcoRV cut CV001-InA-ΔNeoR. The final vector was termed pCEV-GFP-Zeo-01.

5.2 Generation of Universal Wildcard Cell Lines

For the generation of potential wildcard cell lines a CHO cell line adapted to growth in suspension under serum-free conditions and capable to grow to high cell densities (at least $2-5 \times 10^6$ cells/ml) was used. In order to transfect the suspension cells with the target vector pCTV-SAP-Hyg-01 the Nucleofector-technology was used.

Prior to nucleofection the target vector pCTV-SAP-Hyg-01 was digested with SspI for two reasons:

Elimination of unwanted bacterial elements (origin of replication, ampicillin-resistance gene) in order to prevent silencing of target vector mediated by these elements.

Increase the probability of the intact integration of relevant functional elements of the target vector in the genome of the host-cells.

The SspI digestion yielded a 1.698 kb fragment containing the pUC ori and the majority of the AmpR gene. The remaining relevant 7.41 kb target vector element was purified by agarose gel electrophoresis using QIAquick gel extraction kit according to the recommendation of the manufacturer.

For nucleofection with the gel-purified target vector conditions were established that allow high efficient transfection of the suspension adapted CHO-cells. In general efficiencies of 70-90% of transfected cells could be routinely be reached.

The nucleofected cells were allowed to recover for 24 h and then subjected to selection for cells with stable integrated target vector based on expression of Hygromycin phosphotransferase (HygroR) as SM1. For the selection with Hygromycin B (200 μg/ml) the nucleofected cells where transferred to 96-well plates a density that allow the isolation of mono- or oligo-clonal cell populations (limited dilution). This could be done by cell densities between 1-60 cells/well, most preferentially at densities between 1-30 cells/well.

Each of these mono- or oligo-clonal cell populations represents different random integration sites of the target vector. The transcriptional activity of these integration sites was determined by the activity of the hSEAP-reporter gene in the supernatant using a colorimetric microplate assay.

At approximately 70-80% confluence the selected cells were transferred to 24-well plates for further expansion. The supernatant was used for assaying the hSEAP-activity.

The endogenous alkaline phosphatase was inactivated by incubation at 65° C. for 30 min. The activity of hSEAP was measured in hSEAP reaction buffer (2 M diethanolamine, 1 mM $MgCl_2$, 20 mM L-homoarginine, pH 9.8) at 37° C. Hydrolysis of the substrate p-nitrophenol phosphate (120 mM) was measured by OD405 reading. Activity was quantified against a standard with placental alkaline phosphatase.

The majority of the clones showed a very low activity for the hSEAP reporter. Only a fraction of the isolated clones with a stably integrated target vector showed a high expression of the reporter. The typical distribution of the variation in expression levels in these primary clonal or oligo-clonal cell populations is shown by their hSEAP-expression summarized in the examples in FIGS. 7A and B. To identify the rare high-expressing clones termed "outperformer" more than 3000 primary clonal/oligoclonal cell populations were analyzed.

To ensure that the highest expressing clone will be used as universal wildcard cell, a second limited dilution with the clones showing the highest hSEAP-levels was performed in order to identify subclones with the maximum expression level. An example is shown for the clone 01A438 identified in a first limited dilution as outperformer (FIG. 8). Individual cells from clone 01A438 were seeded in a second limited dilution allowing the generation of a single cell derived cell population. As depicted in FIG. 9A and B the resulting subclones displayed in general a higher hSEAP expression compared to the majority of the initial clones from the primary screening. Nevertheless it was possible to identify within this group of high expressing clones, those with the highest expression for hSEAP. At this stage of the selection of clones for further analysis, in addition to the expression level of the reporter gene also the growth capacity (doubling time) of clones was taken into account. Based on this additional criterion the clone 07-022 (marked with an asterisk in FIG. 9) was selected.

In summary, to obtain a host cell line with a high expression level for hSEAP several thousand individual clones were generated by serum-free, limited-dilution cloning. Due to the random integration into the genome only about 50% of these clones displayed measurable expression of hSEAP. From these hSEAP expressing clones only 0.3% of the clones were identified as high expressing clones, i.e. "outperformers" (>25-fold expression over mean of all clones).

5.3 Exchange of the Reporter Gene

For the exchange of the RG1 and the SM1 against a GOI the wildcard cells of subclone 07-022 were cotransfected with an exchange vector pEV-GFP-Zeo-01 according to FIG. 4 and an expression plasmid for the rare cutting homing endonuclease I-SceI. As GOI the coding sequence for a green fluorescent protein (GFP) was used.

The region of the spliceable Intron A in front of the GFP coding region was long enough (1077 bp) to allow efficient homologous recombination, but contains attenuated promoter activity.

The SM1 in the exchange vector is a C-terminal truncated version of the Neomycin-resistance gene (NeoR). Due to a 163 by deletion in the NeoR coding region the resulting truncated Neomycin-phosphotransferase does not confer resistance to G418. The 5' region of the NeoR gene (719 bp) is sufficient to allow homologous recombination with the complete NeoR in the target vector. This strategy allows the activation of the promoterless NeoR gene in the target vector without generating NeoR cells due to random integration of the exchange vector.

The system will allow the selection of those cells which have repaired the homing-enzyme induced DSBs by homologous recombination using the exchange vector as repair-matrix.

As additional selection marker a SM3 (Zeocin resistance gene) is expressed from the GFP-expression cassette by means of an IRES element between the GFP and Zeo resistance gene.

This SM3 is used to determine the frequency of random integration of the exchange vector and to check if other repair events could lead to neomycin-resistant cells without integration of expression-cassette form the exchange vector, just by deletion of the exchange area in the target vector.

To this end the double transfected cells were first selected with G418, the number of generated clones is recorded and clones were analysed for GFP expression by UV-microscopy.

As depicted in FIG. 10 after selection for 11 days with G418 a heterogeneous population of NeoR cells was obtained of which 45-62% showing a bright GFP expression while the remaining of the NeoR cells were GFP-negative.

Those cells could represent either the repair of the DSB by simple endjoining or by one-sided homologous recombination. In the later case only the DSB adjacent to the NeoR-gene is repaired by HR while the DSB adjacent to the CMV-promoter is repaired by non-homologous endjoining.

By means of an additional selection with Zeocin the fraction of GFP-positive cells was increased up to 94% depending on the amount of I-SceI expression plasmid Mnv cotransfected with a constant amount of exchange plasmid (FIG. 11). When using the optimized ratio between the expression vector for the meganuclease and the exchange vector (approach 5 in FIG. 11) a total of 291 colonies expressing GFP were detectable. Based on $2 \times 10^6$ cells plated after transfection and selected with G418 and Zeocin this represents a frequency of $\sim 1 \times 10^{-4}$. This is a surprising good result compared to published frequencies for double strand break induced homologous recombination that are in the range of $1\text{-}2.5\times10^{-6}$.

In summary the use of two selection markers allowed the selection of a homogenous population of cells displaying a bright GFP-fluorescence (FIG. 12).

In addition to the clone 07-022, further wildcard clones were used to demonstrate the exchangeability of the RG1 and SM1 against the expression cassette consisting of GFP-IRES-ZeoR (FIGS. 13 and 14).

In general the exchange using low hSEAP expressing wildcard clones resulted in only non-fluorescent or weak-fluorescent cells after double selection with G418 and Zeocin.

In contrast using high hSEAP expressing wildcard clones resulted in efficient exchange of the expression cassettes by the described meganuclease-mediated exchange mechanism and the generation of double-resistant, bright GFP expressing cells as shown for clone 01-C090 in FIG. 13.

A comparison with the clone 07-022 is shown for the Wildcard-clone 08-018 in FIG. 14. Also with the clone 08-018 it was possible to derive after meganuclease-mediated exchange of expression cassettes a homogenous population of GFP expressing cells. The intensity of the GFP expression was comparable to those seen in cells derived from clone 07-022.

The cells derived from the wildcard cells after the meganuclease based exchange reaction can be expanded in suspension culture under serum-free conditions and used for production purpose.

In order to ensure a single cell derived production cell line the exchanged cells cells could be rapidly generated with a limited dilution approach with reduced effort.

5.4 Molecular Characterisation

To monitor the molecular events during the exchange reaction a PCR based approach using three different primer-combinations (PCR 1-3 see Table 1) used.

TABLE 1

Primer combinations for molecular characterization

| PCR no. | Primer binding 5'-3' | target | Identified phenotype | Size PCR product [bp] |
|---|---|---|---|---|
| 1 | IntA-SEAP | target vector in host wildcard cell | SEAP+, HygroR GFP− | 368 |
| 2 | IntA-GFP | exchange vector | ZeoR GFP (+) | 293 |
| 3 | SV40P-3'Neo | Activated SM2 (NeoR) after homologous recombination | G418+ Zeo+ GFP+ | 971 |

With PCR 1 the stable integrated target vector within the genome of the wildcard-host cell is detected. The PCR 2 is used to confirm the presence of the expression cassette from the exchange vector in cells after performing the exchange reaction. Since the exchange vector can also be incorporated randomly, the PCR 3 is used to confirm homologous recombination at the 3'-end of the exchange-area within the target construct. The 5'-primer for this PCR binds to the SV40 promoter which is present in the exchange construct, while the 3'-primer binds to the 3' part of the NeoR-gene present only in the target-construct and not in the exchange construct. Only after activation of the promoterless SM2 (NeoR-gene) by homologous recombination the PCR 3 can generate a 971 by PCR-product.

By combination of the results from the different PCR-analysis the elimination of the expression cassette from the target construct and introduction of the expression cassette from the exchange vector can be demonstrated.

The results for such an analysis are summarized in FIG. 15 for three different, universal wildcard cell lines for which an exchange reaction was successfully performed. In part (A.) the presence of the target construct was confirmed by primers binding in the intron of the CMV-promoter-element and the 5'-region of the hSEAP CDS. Panel (B.) shows the confirmation of the stable integrated expression cassette of the exchange vector B by the same intron primer as in (A.) in combination with a primer that binds in the 5'-region of the CDS for GFP. The successful amplification of corresponding PCR-product indicates the introduction of the expression cassette either by HR or by random integration. Panel (C.) displays the PCR-confirmation of the presence of an activated NeoR gene in the target vector as the result of HR with the exchange vector. Since the primers for this PCR bind to the SV40 promoter (5'-primer), which is present only in the exchange vector and to the 3'-part of the NeoR-CDS (3'-primer), present only in the target vector, successful amplification indicates HR between the exchange vector and the target vector at the 3'-I-SceI mediated DSB.

As positive control (lane 8) in panel (A.) and (B.) the target vector and the exchange vector 2 have been used, respectively. The positive control in panel (C.) consists of a vector (CV001) with identical primer binding sequences but with a slightly different distance to another. Therefore the positive control results in a slightly smaller PCR-product (917 by instead of 971 bp) than expected from the genomic DNA. As negative control either the template DNA has been replaced by water (lane 9) or, to check for unspecific amplification from CHO-genomic DNA, by the same amount of DNA from the parental CHO-cell line without nucleofection of the target construct (lane 10).

The clone 07-022 was most intensively been characterized and in addition to the starting cells and it's derivates of successful exchange cells, also a control for random integration of the exchange vector B was analyzed. The cell clone used for this control showed after nucleofection of only the exchange vector B resistance to Zeocine and a very weak GFP-fluorescence.

For the clones 08-018 and 01C090 the starting cells and successfully exchange cells that survived the double selection and display a bright GFP-fluorescence were analyzed.

For all clones the presence of the hSEAP-CDS could be demonstrated clearly in the starting cell population (panel A). For clone 07-022 the presence of this CDS could also be confirmed for the cell clone generated by random integration. After the meganuclease-mediated exchange reaction the hSEAP-CDS was no longer amplifiable in all of the tested exchanged clones showing NeoR/ZeoR and a bright GFP-fluorescence. This indicates the elimination of the initial expression cassette from the integrated target vectors in all analyzed examples.

In accordance with that finding also the presence of the expression cassette form a the exchange vector B could be demonstrated by PCR for the GFP-CDS only after performing the exchange reaction (panel B lanes 3, 5, 7). The starting cells for the tested clones were negative in this PCR-assay (panel B, lanes 1, 4, 6). This PCR-assay is not specific to introduction of the GFP-expression cassette by HR. The example for random integration of the exchange vector B from clone 07-022 showed that also here a positive signal could be obtained with the GFP-CDS specific primer.

The bright intensity of the GFP-expression in the different cell populations derived after performing the exchange reaction indicates, that introduction of the GFP-CDS had occurred in the tagged expression-hot spot within the cells used in lane 3, 5 and 7.

To finally confirm that the observed phenotype is based on the elimination of the expression cassette in the target vector and introduction of the expression cassette from the exchange vector at the same position, an additional PCR-analysis was performed (panel C.) This PCR will give only an expected PCR-product of 971 by when the 3' I-SceI mediated DSB in the target vector has been repaired by HR using the exchange vector 2 as repair matrix. As expected only in the double resistant, bright-GFP cells an expected PCR-product could be detected (panel C., lane 3, 5, 7) and not in the cells resulting from random integration of the exchange vector (panel C., lane 2).

The invention claimed is:

1. A method for the generation of a high producer host cell for the production of recombinant gene products comprising the following steps:
   (a) providing a target vector comprising:
      (i) a first vector portion comprising a reporter gene (RG1) operatively linked to a first expression control sequence comprising a constitutive promoter (P1),
      (ii) a second vector portion comprising a first selection marker gene (SM1) operatively linked to a second expression control sequence (P2),
      (iii) a third vector portion comprising a second non-functional selection marker gene (SM2) without operative linkage to an expression control sequence, wherein the first vector portion is located in the 5'-position, the second vector portion is located between the first vector portion and the third vector portion, and the third vector portion is located in the 3'-position, and
      (iv) a first and a second recognition site for a double-strand break mediating enzyme, wherein the first recognition site is located between the first expression control sequence (P1) and the first reporter gene (RG1) and the second recognition site is located between the second vector portion and the third vector portion, the double-strand break mediating enzyme being a meganuclease or a homing nuclease, and wherein the first and second recognition sites are recognized by the same double-strand break mediating enzyme,
   (b) introducing the target vector in a host cell under conditions in order to allow random integration of the target vector into the genome of the host cell,
   (c) selecting a host cell having stably integrated the target vector and showing high transcriptional activity of the reporter gene (RG1),
   (d) providing an exchange vector comprising:
      (i) a gene of interest (GOI), and
      (ii) an inactive second selection marker gene (ΔSM2) operatively linked to a third expression control sequence (P3),
      wherein the exchange vector comprises a first 5'-homologous sequence and a second 3'-homologous sequence, which allow recombination with sequences of the target vector,
   (e) introducing the exchange vector into a host cell obtained in step (c) under conditions to allow a double strand break at the first and/or second recognition site as defined in step (a)(iv) and an integration of the exchange vector into the genome of the host cell by double-strand break-mediated homologous recombination, whereby the inactive second selection marker gene (ΔSM2) is activated by an integration of the exchange vector by homologous recombination with the target vector,
   (f) selecting a high producer cell having integrated the exchange vector by homologous recombination with the integrated target vector, wherein the producer cell expresses the GOI.

2. The method of claim 1, wherein the host cell is a eukaryotic cell.

3. The method of claim 1, wherein the reporter gene (RG1) encodes an enzyme or a luminescent or fluorescent gene product.

4. The method of claim 1, wherein the first expression control sequence (P1) comprises a constitutive promoter.

5. The method of claim 1, wherein the double-strand break mediating enzyme is a meganuclease or a homing nuclease having a recognition site of at least 10.

6. The method of claim 1, wherein a cell is selected having the target vector integrated as a single copy into a single site of the chromosome of the host cell.

7. The method of claim 1, wherein the selecting step (c) is based on a detection of the first selection marker gene (SM1) activity.

8. The method of claim 1, wherein the gene of interest (GOI) lacks a functional expression control sequence.

9. The method of claim 1, wherein the exchange vector comprises the incomplete second selection marker gene (ΔSM2) operatively linked to a third expression control sequence (P3).

10. The method of claim 1, wherein the first 5'-homologous sequence has a length of at least about 1000 nucleotides and/or the second 3'-homologous sequence has a length of at least about 700 nucleotides.

11. The method of claim 1, wherein the exchange vector additionally comprises:
   a negative selection marker gene.

12. The method of claim 9, wherein the third expression control sequence (P3) is a constitutive promoter.

13. The method of claim 2, wherein the host cell is a mammalian cell.

14. The method of claim 13, wherein the host cell is a CHO cell.

15. The method of claim 4, wherein the constitutive promoter is a CMV promoter.

16. The method of claim 15, wherein the CMV promoter comprises an intron A sequence.

17. The method of claim 1, wherein the double-strand break mediating enzyme is selected from the group consisting of I-SceI, I-SceII, I-Scan, I-SceIV, I-CeuI, I-CreI, I-PpoI, I-TevI, I-TevII, I-TevIII, HO and Endo SceI.

18. The method of claim 5, wherein the double-strand break mediating enzyme is a meganuclease or a homing nuclease having a recognition site of at least 12 nucleotides.

19. The method of claim 5 wherein the double-strand break mediating enzyme is a meganuclease or a homing nuclease having a recognition site of at least 18 nucleotides.

20. The method of claim 1, wherein the gene of interest (GOI) comprises a partial expression control sequence which is substantially identical to a 3'-portion of the first expression control sequence in the target vector.

21. The method of claim 1, wherein the exchange vector additionally comprises a third selection marker located outside the sequence defined by the first 5'-homologous sequence and second 3'-homologous sequence.

22. The method of claim 21, wherein the third selection marker is a suicide gene.

23. The method of claim 22, wherein the suicide gene is HSV thymidine kinase.

\* \* \* \* \*